United States Patent [19]

Buchanan et al.

[11] Patent Number: 6,077,945

[45] Date of Patent: Jun. 20, 2000

[54] PROCESS FOR MAKING ALKYLPOLYGLYCOSIDES

[75] Inventors: Charles Michael Buchanan, Kingsport; Matthew Davie Wood, Gray, both of Tenn.

[73] Assignee: Eastman Chemical Company, Kingsport, Tenn.

[21] Appl. No.: 09/019,746

[22] Filed: Feb. 9, 1998

Related U.S. Application Data

[60] Provisional application No. 60/039,575, Feb. 18, 1997.

[51] Int. Cl.$^7$ .............................. C07H 1/00; C08B 37/00
[52] U.S. Cl. ..................... 536/18.6; 536/18.5; 536/120; 536/124; 536/4.1
[58] Field of Search ............................ 536/18.5–18.6, 536/4.1, 124, 120

[56] References Cited

U.S. PATENT DOCUMENTS

| | | | |
|---|---|---|---|
| 3,375,243 | 3/1968 | Nevin | 260/610 |
| 3,547,828 | 12/1970 | Mansfield | 252/351 |
| 3,565,885 | 2/1971 | Molotsky | 260/210 |
| 3,772,269 | 11/1973 | Lew | 260/210 |
| 3,839,318 | 10/1974 | Fujita | 260/210 |
| 4,393,203 | 7/1983 | Mao | 536/124 |
| 4,465,828 | 8/1984 | Rau | 536/18.6 |
| 4,557,729 | 12/1985 | McDaniel | 8/111 |
| 4,704,453 | 11/1987 | Lorenz | 536/18.6 |
| 4,713,447 | 12/1987 | Letton | 536/18.6 |
| 4,889,925 | 12/1989 | Schmid | 536/18.6 |
| 4,898,934 | 2/1990 | Hofmann | 536/18.6 |
| 4,904,774 | 2/1990 | McDaniel | 536/127 |
| 4,939,246 | 7/1990 | Baur | 536/18.6 |
| 4,990,605 | 2/1991 | Lueders | 536/18.5 |
| 5,003,057 | 3/1991 | McCurry | 536/18.6 |
| 5,104,981 | 4/1992 | Yamamuro | 536/18.6 |
| 5,166,337 | 11/1992 | Ripke | 536/126 |
| 5,304,639 | 4/1994 | Gibson | 536/4.1 |
| 5,362,861 | 11/1994 | Beaulieu | 536/4.1 |
| 5,430,131 | 7/1995 | McCurry | 536/18.5 |
| 5,432,269 | 7/1995 | Borsotti | 536/18.6 |
| 5,432,275 | 7/1995 | Beaulieu | 536/124 |
| 5,449,763 | 9/1995 | Wulff et al. | 536/18.6 |
| 5,459,249 | 10/1995 | Bergfeld | 536/18.6 |
| 5,461,144 | 10/1995 | Kahsnitz | 536/18.6 |
| 5,478,931 | 12/1995 | Ripke | 536/124 |
| 5,480,978 | 1/1996 | Johannisbauer | 536/4.1 |
| 5,480,979 | 1/1996 | Weuthen | 536/18.6 |
| 5,612,467 | 3/1997 | Weuthen | 536/18.6 |
| 5,631,357 | 5/1997 | Weuthen | 536/18.6 |

FOREIGN PATENT DOCUMENTS

| | | |
|---|---|---|
| 0 570 056 A1 | 11/1993 | European Pat. Off. . |
| 9307160 | of 1993 | WIPO . |
| 9402494 | of 1994 | WIPO . |
| 9409019 | of 1994 | WIPO . |

OTHER PUBLICATIONS

M.Weuthen, et al, *Fett Wiss. Technol.* 97(6), 209–11 (1995), (Abstract #1).
DE 3940827 (1991), Hammelstein, (Abstract #2).
DE 4140332 (1993), Carduck, (Abstract #3).
EP 411477 (1991), Foerg, (Abstract #4) (German language patent listed above and enclosed).
EP 514628 (1992), Ripke, (Abstract #5).
EP 526710 (1993), Ripke, (Abstract #7).
EP 569682 (1993), Balzer & Ripke, (Abstract #8).
JP 04295490 (1992), (Abstract #9).
JP 04308599 (1992), (Abstract #10).
DE 4340015 (1995), Breitzke, (Abstract #11).

*Primary Examiner*—James O. Wilson
*Assistant Examiner*—Howard Owens
*Attorney, Agent, or Firm*—Jonathan D. Wood; Cheryl J. Tubach; Harry J. Gwinnell

[57] ABSTRACT

A novel process for making an alkylpolyglycoside comprises reacting a monosaccharide with an alcohol in the presence of a binary sulfate catalyst under heat. The particular binary sulfate catalyst is a mixture of $H_2SO_4$ and inorganic base at a normal ratio of about 0.7:1 to 1.1:1 of $H_2SO_4$ to inorganic base. Also the alkylpolyglycoside product from the reaction mixture can be isolated so that the alkylpolyglycoside process contains less than 5 weight percent free alcohol, and further separated into a white, free flowing powder of high DP (degree of polymerization) alkylpolyglycoside and a low DP alkylpolyglycoside paste.

18 Claims, No Drawings

PROCESS FOR MAKING ALKYLPOLYGLYCOSIDES

CROSS-REFERENCE TO RELATED APPLICATION

This application claims the benefit of U.S. Provisional Application Ser. No. 60/039,575, filed Feb. 18, 1997.

FIELD OF THE INVENTION

The present invention relates to alkylpolyglycosides. More specifically the present invention relates to a catalyzed process of making alkylpolyglycoside from monosaccharide and alcohol. More specifically, the present catalyzed alkylpolyglycoside process relates to a simplified process of making alkylpolyglycoside wherein no neutralization or bleaching is required for providing a high quality alkylpolyglycoside product.

BACKGROUND OF THE INVENTION

Alkyl polyglycosides (alkylpolyglycoside) are nonionic surfactants prepared by glycosidation of a source of a carbohydrate with an alcohol. alkylpolyglycoside contain one or more monosaccharide units and an alkyl side chain. Alkyl polyglycosides have the general structure:

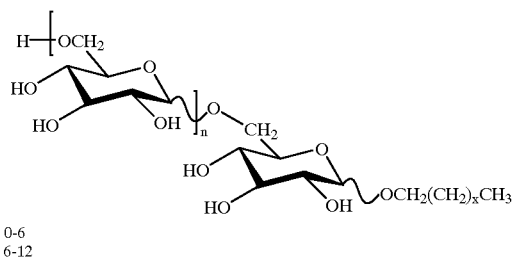

$n = 0-6$
$x = 6-12$

The term "alkylpolyglycoside", as used herein, includes alkyl monoglycosides, alkyl oligoglycosides (2–10 sugar units), and alkyl polyglycosides. The average alkyl chain length results from the alcohol feedstock, the particular synthetic method employed, and the extent to which the reaction is driven to completion. The degree of saccharide polymerization (DP) is due to the fact that monosaccharides also contain a primary hydroxyl at the $C_6$ position. alkylpolyglycoside having a DP less than 2 are preferred for good surfactant surface tension.

Alkylpolyglycosides are typically prepared by reacting monosaccharide such as glucose or a monosaccharide source such as dehydrated starch syrup with a long chain primary alcohol in the presence of a strong acid catalyst. The known two-stage process involves the following basic steps: 1) acid catalyzed glycosidation reaction of a monosaccharide source with butanol to form butyl glycoside, with removal of water formed during the reaction, 2) transglycosidation of the butyl glycoside with a $C_8$ to $C_{20}$ alcohol to form the long (alkyl) chain alkylpolyglycoside, with removal of the butanol, 3) neutralization of the acid catalyst, 4) distillation to remove unreacted long chain alcohol, 5) bleaching to improve the color and odor of the product and 6) isolation of the alkylpolyglycoside. The glycosidation and transglycosidation reactions are equilibrium controlled until the catalyst is neutralized.

The typical single-stage alkylpolyglycoside process involves all of the steps of the two-stage process, with the exception of the consolidation of steps 1) and 2) shown above by directly reacting glucose with a long chain alcohol.

The commonly preferred known catalysts for the two-stage process are sulfuric acid and p-toluene-sulfonic acid, as disclosed in U.S. Pat. Nos. 3,772,269, and 3,375,243. It is a generally known that strongly acidic reaction conditions are required for successful glycosidation. Favored catalysts for single-stage processes have been long chain alkyl sulfonic acids since they have improved solubility with both the carbohydrate and alcohol. For example, see U.S. Pat. No. 5,459,249. It is known that choice of catalyst is critical both to the color and the DP of the final alkylpolyglycoside product.

Alkylpolyglycoside glycosidation reactions catalyzed by strong acids such as sulfuric acid suffer from two main sources of color formation. Firstly, the strong acid catalyst promotes dehydration of the monosaccharide. For instance, when the monosaccharide is glucose, dehydration leads to highly colored furan derivatives such as furfuraldehyde. Secondly, the strongly acidic (pH of about 1.0) acid catalyzed reactions must be neutralized with a strong base in order to terminate the reaction. While the addition of base is necessary to stop the glycosidation equilibrium reaction, the neutralization reaction promotes unavoidable formation of color via the well known "peeling reactions".

U.S. Pat. No. 5,432,269 discloses binary catalysts formed from a strong organic acid and a weak organic base that provide improved alkylpolyglycoside color. However, the reaction medium is still strongly acidic throughout the reaction period. The reaction medium must be neutralized at the end of the reaction. In addition to raising the pH of the reaction medium, neutralization also liberates the organic base which must be removed by distillation. Unfortunately, neutralization also leads to color formation.

U.S. Pat. No. 4,898,934 discloses the addition of alkali salts of inorganic acids or polybasic saturated carboxylic acids to the reaction mixture containing an acid such as sulfuric acid. The additives are reported to act as complexing agents. The acid must still be neutralized at the completion of the reaction. The addition of base promotes unavoidable side reactions, namely, "peeling reactions" which contribute to excess color formation.

U.S. Pat. No. 4,465,828 discloses the addition of hydroxy-carboxylic acids to the reaction mixture as a means of decreasing color formation in the production of alkylpolyglycoside. The carboxylic acid reportedly serves as an acid buffer.

U.S. Pat. No. 4,704,453 discloses the complete neutralization of an acid such as $H_2SO_4$ with an equivalent or excess amount of sodium metaborate, borax, or sodium perborate. Boric acid is thereby generated from sulfuric acid. The boric acid is disclosed to complex with glucose, forming a Lewis acid catalyst, which is the actual reaction catalyst. However, the borate salts formed by that reaction must be removed from the reaction medium.

The commonly preferred means of alkylpolyglycoside color reduction are bleaching with 30% aqueous peroxide, as disclosed in WO 9003077, WO 9402494, U.S. Pat. No. 5,432,275, and U.S. Pat. No. 5,362,861; bleaching with an aqueous solution of ozone, as disclosed in EP 569682, DE 3940827, and EP 389753; and reduction with boranates, as shown in U.S. Pat. No. 5,104,981, and U.S. Pat. No. 5,430,131.

In alkylpolyglycoside glycosidation, the isolation step has also been the subject of much research. The vast majority of the time, the product is isolated and packaged as an aqueous solution. However, a number of research groups have attempted to find conditions for isolating the alkylpolyglycoside as a solid or in a highly purified form by extraction because of the increased cost of transporting aqueous solutions and the formulation constraints which are associated with isolation of products as aqueous solutions. U.S. Pat. No. 3,547,828 discloses an acetone extraction method in which a crude alkylpolyglycoside mixture is fractionated into a solid high DP fraction (DP equal to or greater than 2), which is isolated by filtration or centrifuging, and a viscous liquid composed primarily of alkylmonoglycoside (a low DP fraction having a DP less than 2) plus excess alcohol and acetone. In order to isolate the low DP alkylpolyglycoside from the acetone fraction, excess free alcohol and acetone are distilled away. Distillation, of course, leads to discoloration of the low DP alkylpolyglycoside. Distillation can be avoided by removing the acetone by simple distillation and recycling the alcohol/low DP alkylpolyglycoside back to the reaction vessel. Recycling lowers the overall yield of the reaction and the low DP alkylpolyglycoside is not available for use as a surfactant.

In light of the above, it would be desirable to have an easier, more efficient process for producing and isolating low color alkylpolyglycoside. It would be particularly desirable to provide such a process wherein the color and odor reduction step is completely avoided. It would be further desirable if such process included an efficient, high yield method of isolating the alkylpolyglycoside formed and separating the alkylpolyglycoside product into a solid or near solid, high DP alkylpolyglycoside component and a solid or near solid low DP alkylpolyglycoside component.

SUMMARY OF THE INVENTION

In the present invention, a process for making alkylpolyglycoside comprises reacting a monosaccharide with an alcohol having from 2 to 50 carbon atoms selected from the group consisting of primary alcohols, secondary alcohols, and a mixture thereof in the presence of a binary sulfate catalyst under heat. The binary sulfate catalyst comprises a normal ratio of $H_2SO_4$ to inorganic base of about 0.7:1 to 1.1:1. An alkylpolyglycoside product is formed.

The present invention further includes a process for isolating and separating an alkylpolyglycoside product which is preferably prepared in the absence of a base. The alkylpolyglycoside product is isolated by removing a sufficient amount of unreacted alcohol thereby forming a waxy alkylpolyglycoside product containing less than 5 weight percent free alcohol. The waxy alkylpolyglycoside product is separated into a high DP and low DP alkylpolyglycoside by heating the waxy alkylpolyglycoside product at a temperature between about 50 to 100° C. to form a viscous melt; adding a nonsolvent under high shear, thereby precipitating a high DP alkylpolyglycoside solid component from a soluble fraction; and removing the solid high DP alkylpolyglycoside component from the soluble fraction.

The present invention still further includes a grinding process for separating the waxy alkylpolyglycoside product containing less than 5 weight percent free alcohol. The waxy alkylpolyglycoside product is ground in the presence of a nonsolvent, thereby precipitating high DP alkylpolyglycoside solid component from a soluble fraction. Thereafter, the high DP alkylpolyglycoside solid component is removed from the soluble fraction.

DETAILED DESCRIPTION OF THE INVENTION

In the process of the present invention alkylpolyglycoside glycosidation/transglycosidation reactions are unexpectedly carried out effectively using a particular binary sulfate catalyst that is substantially less acidic than sulfuric acid, in contrast to the aforementioned references. In addition, the use of the binary sulfate catalyst provides the benefit of a glycosidation reaction with highly reduced color and odor formation.

The mildly acidic to near-neutral pH level of the reaction medium of the present process enables the reaction to be carried out sufficiently without the requirement for an acid neutralization step. In the preferred absence of neutralizing base, the present reaction provides significant unexpected benefits. Firstly, the increase in color caused directly by the addition of strong base is eliminated. In previous methods wherein the catalyst had to be completely neutralized with base, the distillation of excess alcohol away from alkylpolyglycoside in the presence of base lead to significant discoloration of the alkylpolyglycoside. However, when no base is used in the present process, the unreacted free alcohol can be almost completely removed from the alkylpolyglycoside without color formation.

Secondly, the waxy alkylpolyglycoside product can be efficiently isolated and separated into high DP, alkylpolyglycoside powder and a highly concentrated low DP alkylpolyglycoside paste at a much higher yield than has been previously possible. Most of the excess alcohol is distilled away prior to separating the high and low DP alkylpolyglycoside from each other eliminating the need to distill away excess alcohol after separation. Therefore, the present process provides a way of obtaining a high yield of a concentrated form of the desirable low DP alkylpolyglycoside.

Although the rate of reaction of the present process is somewhat slower than a $H_2SO_4$ catalyzed reaction, the benefit of color reduction, the elimination of a separate color and odor reduction step, the lack of acid neutralization, and a higher product yield makes the present process significantly better than previously used alkylpolyglycoside glycosidation processes.

The alkylpolyglycoside formation process of the present invention comprises reacting a monosaccharide with an alcohol having from 2 to 50 carbon atoms selected from the group consisting of primary alcohols, secondary alcohols, and a mixture thereof in the presence of a binary sulfate catalyst under heat. The binary sulfate catalyst is a mixture of $H_2SO_4$ and inorganic base. The normal ratio of $H_2SO_4$ to inorganic base is about 0.7:1 to 1.1:1. A critical aspect of the process of the present invention is the use of the binary sulfate catalyst.

The binary sulfate catalyst of the present invention is a mixture of compounds formed by the partial neutralization of $H_2SO_4$ with the inorganic base. The compounds formed by the binary system are represented by the formula $M_{(x+z)}H_{(y-z)}SO_4$, wherein the summation of (x+z) and (y-z) is 2. The preferred inorganic bases suitable for use in the binary sulfate system are LiOH, NaOH, KOH, $Na_2CO_3$, $K_2CO_3$, and $Li_2CO_3$. The more preferred base is NaOH.

The binary sulfate catalyst of the present invention is the mixture of $H_2SO_4$ and inorganic base at a normal ratio of about 0.7:1 to 1.1:1, respectively. The preferred binary sulfate catalyst system has a normal ratio of about 0.85:1 to 1:1 of $H_2SO_4$ to inorganic base, with a normal ratio of about 0.9:1 to 1:1 being most preferred.

The concentration of binary sulfate catalyst in the process of the present invention preferably provides a reaction pH ranging between about 4 to about 6.5. The more preferred pH of the reaction medium is in the range of about 4.5 to 6.0.

The binary sulfate catalyst can be prepared in situ or it can be pre-formed outside of the reaction environment. In the in situ preparation, the catalyst is prepared by dissolving the appropriate amount of base in a portion of alcohol before adding the required portion of $H_2SO_4$. In the case of pre-formed binary sulfate catalyst, the catalyst is added in the form of $MHSO_4$, where M is a metal selected from the group consisting of Li, Na, or K. The preferred pre-formed catalyst is $NaHSO_4$.

Although neutralization of catalyst is not necessary in the practice of this invention, appropriate bases can be utilized to render the reaction medium more basic prior to distillation to remove alcohol. The preferred bases for complete neutralization of catalyst include NaOH, KOH, sodium butoxide, MgO, $Mg(OAc)_2$, NaOAc, KOAc, NaOPr, KOPr, NaOBu, and KOBu. The most preferred bases for neutralization are MgO, $Mg(OAc)_2$, NaOH, NaOAc, and KOAc.

In the process of the present invention, a broad spectrum of monosaccharides, and mixtures of different monosaccharides can be utilized. Suitable examples of monosaccharides include glucose, mannose, galactose, talose, altrose, lyose, arabinose, xylose, ribose, fructose, ribose, and the like, and a mixture thereof. Compounds hydrolyzable to monosaccharides may also be employed, and are herein included in the definition of the term "monosaccharide." Examples include starch, cellulose, sucrose, lactose, maltose, and the like. In the single stage reaction process, preformed glycosides can also be utilized. For example, methyl glycoside, propyl glycoside, butyl glycoside, ethyl-1-ol glycoside, and the like are all suitable substrates. The preferred monosaccharide is glucose due to its low cost, availability, and good reactivity. The glucose used can be in the form of corn syrup, glucose monohydrate, or anhydrous glucose. The most preferred glucose is anhydrous glucose in the form of a fine powder.

The effective molar ratio of catalyst material to monosaccharide is preferably about 0.001:1 to about 0.5:1. The more preferable molar ratio is about 0.006:1 to about 0.2:1, with about 0.008:1 to about 0.018:1 being most preferred. However, it should be understood that the preferred ratio of catalyst material to monosaccharide depends upon the exact normal composition of the catalyst formed in the reaction mixture. When the normal ratio of $H_2SO_4$ to inorganic base is from about 0.85:1 to about 0.95:1, the catalyst is less active relative to $MHSO_4$ and a greater concentration of catalyst is required to achieve an equivalent rate of reaction.

The alcohols useful in the process of the present invention are monohydric or polyhydric primary or secondary alcohols having from 2 to about 50 carbon atoms. The alcohols may be straight or branched alcohols, saturated or unsaturated alcohols, alkyl or aralkyl alcohols, ether alcohols, cyclic alcohols, or heterocyclic alcohols. The only requirement is that the alcohol be capable of alkylating the monosaccharide at the $C_1$ position. The preferred monohydric alcohols are primary, aliphatic alcohols having the general formula ROH wherein R is linear or branched and is selected from the group consisting of alkyl groups having about 4 to 18 carbon atoms, alkenyl groups having about 4 to 18 carbon atoms, and a mixture thereof. Typical examples of the preferred monohydric alcohol are n-butanol, i-butanol, caporic alcohol, caprylic alcohol, octyl alcohol, nonyl alcohol, decyl alcohol, dodecyl alcohol, tridecyl alcohol, tetradecyl alcohol, pentadecyl alcohol, hexadecyl alcohol, stearyl alcohol, oleyl alcohol, elaidyl alcohol, petroselinyl alcohol, arachyl alcohol, behenyl alcohol, and erucyl alcohol, as well as their mixtures.

An additional example of preferred monohydric alcohols are those represented by the formula:

$HO(CHXCH_2O)_nCH_2CH_2OR^1$ wherein the alkyl group, $R^1$, can have from 1 to about 20 carbon atoms, X is hydrogen or an aliphatic group having from 1 to about 10 carbon atoms, and n is an integer from 0 to about 20. The most preferred monohydric alcohols of this type are when $R^1$ has from about 8 to about 16 carbon atoms, X is hydrogen or methyl, and n is from about 0 to about 10. Examples of such monohydric alcohols include mono-methyl polyethylene glycol and mono-methyl polypropylene glycol.

Polyhydric alcohols are also useful in the present process. Examples of preferred polyhydric alcohols include ethylene glycol, propylene glycol, polyethylene glycol, polypropylene glycol, butylene glycol, and polybutenyl glycol. The most preferred polyhydric alcohols are ethylene glycol and propylene glycol.

The effective molar ratio of alcohol to monosaccharide in the reaction mixture is preferably about 1.5:1 to about 10:1, alcohol to monosaccharide. The preferred molar ratio is between about 3:1 to about 6:1 alcohol to monosaccharide.

When operating the process in two stages, a short chain alcohol having 2 to about 4 carbon atoms is reacted with the monosaccharide in the first stage. The initial molar ratio of the short chain alcohol to monosaccharide is preferably between about 3:1 to about 6:1. $C_2$- to $C_4$-alkylpolyglycoside is formed in the first stage. After the monosaccharide disappears during the initial stages of the reaction, the unreacted short chain alcohol is removed by vacuum distillation along with any water formed during the reaction. Simultaneously with removal of the unreacted short chain alcohol, a long chain alcohol having about 8 to 50 carbon atoms is added. The long chain alcohol is then reacted with the short alkyl chain alkylpolyglycoside and any unreacted monosaccharide present, if any. The molar ratio of long chain alcohol reacted with the $C_2$- to $C_4$-alkylpolyglycoside (including any unreacted monosaccharide) is between about 3:1 to about 6:1 alcohol to short chain alkylpolyglycoside, most preferably between about 3:1 to about 5:1. The rate of addition of the long chain alcohol is equal to, or faster, than the rate at which the short chain alcohol is removed. Thus, the exact molar ratio of short and long chain alcohol varies according to the stage of the reaction.

For the present process operating in a single stage, all of the alcohol is typically present at the beginning of the reaction unless a portion of the alcohol is utilized to add the glucose as a slurry. The single stage reaction alcohol is preferably a $C_8$ to $C_{50}$ alcohol. Although all of the monosaccharide can be added to the alcohol in one portion, the preferred method is to add a portion of the monosaccharide with the catalyst material. After the initial monosaccharide reacts and disappears, the remaining monosaccharide is added in stages so that the amount of unreacted monosaccharide is kept low. The initially formed alkylpolyglycoside in the reaction mixture serves to help solubilize the monosaccharide added during the latter reaction stages. Therefore, as with the two-stage process, the exact molar ratio of monosaccharide and long chain alcohol varies according to the stage of the reaction.

A broad reaction temperature range from about 90 to about 150° C. can be used in the practice of this invention. At lower temperatures, the reaction rate can be too slow. At higher temperatures the DP of the product can become too high. Hence, a more preferred reaction temperature range is from about 105 to about 130° C. The most preferred reaction temperature range is from about 110 to about 120° C. Pressure is not critical in the present process.

Following alkylpolyglycoside formation via the process of the present invention, it is necessary to isolate the alkylpolyglycoside from the reaction mixture. First, the reaction mixture may be filtered to remove any solids present. The excess unreacted alcohol can then be removed by distillation. The preferred means for distilling away the alcohol is by means of a falling film evaporator, a wiped film evaporator, or a combination of a wiped film and falling film evaporator. The preferred temperature and pressure for a falling or wiped film evaporator is a temperature range from about 80 to about 200° C. at a vacuum of from about 0.001-mm Hg to about 20-mm Hg. The preferred temperature and pressure ranges are from about 120 to about 170° C. at a vacuum of from about 0.02-mm Hg to about 2-mm Hg. It should be understood that the exact conditions depend upon the boiling point of the alcohol being removed.

In removing the excess alcohol, preferably the DP of the alkylpolyglycoside product is not significantly increased since an increase in DP is often accompanied by increase in color. However, increasing the DP of the alkylpolyglycoside product with no negative impact on color is possible by operating the distillation system at higher temperatures and longer contact times. That is, the concentration of the monoglycoside decreases in the alkylpolyglycoside mixture while the amount of di-, tri-, and higher glycosides increase. An increase in the mole percentage of high DP alkylpolyglycoside in the alkylpolyglycoside solution increases the viscosity of the alkylpolyglycoside solution much more than would a similar increase in the mole percentage of monoglycoside. Hence, these high quality, high DP alkylpolyglycoside are useful as viscosity modifiers in personal care applications.

The present invention further includes an additional process for isolating the alkylpolyglycoside product, which is preferably prepared in the absence of base, from the reaction mixture and separating the high DP alkylpolyglycoside component from the low DP alkylpolyglycoside. This isolation and separation process results in a solid, high DP alkylpolyglycoside powder and a low DP alkylpolyglycoside paste. In the process, a sufficient amount of excess alcohol is first removed from the alkylpolyglycoside product so that the alkylpolyglycoside product contains less than about 5 weight percent free alcohol, thereby forming an essentially waxy alkylpolyglycoside solid. The excess alcohol is preferably removed by distillation as discussed above. When distillation of alcohol is not in the presence of base, significant discoloration of alkylpolyglycoside does not occur, providing an added benefit of the present invention. Previous alkylpolyglycoside processes requiring addition of base for neutralization of a strongly acidic catalyst required further steps for bleaching the alkylpolyglycoside.

After isolating the alkylpolyglycoside product by removing most of the excess alcohol, the process of the present invention comprises separating the low DP alkylpolyglycoside component of the alkylpolyglycoside product from the high DP alkylpolyglycoside component. The waxy alkylpolyglycoside solid is heated to a temperature of about 50 to about 100° C. to form a viscous melt of the alkylpolyglycoside product. Then a nonsolvent, with respect to the high DP alkylpolyglycoside, is added to the resulting viscous alkylpolyglycoside melt under high shear. This nonsolvent is a solvent which promotes the precipitation or crystallization of high DP alkylpolyglycoside over low DP alkylpolyglycoside in alcohol. One suitable nonsolvent is acetone. The nonsolvent mixing temperature is preferably chosen to be essentially the same as the boiling point of the nonsolvent. The mixing of the nonsolvent in the alkylpolyglycoside melt causes high DP alkylpolyglycoside to precipitate away from the soluble fraction as a solid component. The high DP alkylpolyglycoside solid component is removed from the soluble fraction by any sufficient method known in the art to provide a free-flowing powder. When the isolation occurs in the absence of base, the separation results in a free-flowing powder that is white. The remaining soluble fraction contains low DP alkylpolyglycoside, a minor amount of excess alcohol, and nonsolvent. The nonsolvent is thereafter driven away by further distillation leaving a paste containing the low DP alkylpolyglycoside in a minor amount of alcohol. Thus, the process preferably results in a free flowing, white powder of high DP alkylpolyglycoside and a low DP alkylpolyglycoside paste.

Alternatively, after the excess free alcohol has been removed to less than 5 weight percent, the waxy alkylpolyglycoside product may be separated into its high and low DP components by grinding in the presence of a nonsolvent, such as acetone. Grinding of the waxy alkylpolyglycoside product may be conducted using a number of different types of equipment such as a Waring blender. Preferably, the waxy alkylpolyglycoside is substantially cooled during the grinding by the addition of cooling agents such as dry ice or by external cooling. The mixing of the nonsolvent in the ground alkylpolyglycoside causes high DP alkylpolyglycoside to crystallize and separate from the soluble fraction. The high DP alkylpolyglycoside is removed from the soluble fraction. The remaining soluble fraction contains low DP alkylpolyglycoside, a minor amount of excess alcohol, and nonsolvent. The nonsolvent is thereafter driven away by further distillation leaving the low DP alkylpolyglycoside in a paste form. Thus, this process variation results in a white powder of an alkylpolyglycoside having a high DP and a paste of an alkylpolyglycoside having a low DP. Further, if desired, the low DP alkylpolyglycoside may be recycled to the reaction vessel, blended with other alkylpolyglycoside, or used for further chemical modification.

The glycosidation process of the present invention provides a very low color waxy solid alkylpolyglycoside containing both high and low DP alkylpolyglycoside. This solid waxy alkylpolyglycoside product is stable during storage, offering a distinct advantage over aqueous alkylpolyglycoside solutions both in shipping and in storage through reduced weight and volume. From this waxy alkylpolyglycoside product, the isolation process of the present invention further provides an unexpectedly high yield of very low color, low DP alkylpolyglycoside paste and a white, free flowing powder of high DP alkylpolyglycoside. Thus, the present invention provides alkylpolyglycoside that can be used as the essentially waxy solid itself or it can be isolated and separated into low polydispersity range polymers for more particular surfactant applications. The low DP alkylpolyglycoside generally has a higher surface tension and has higher water solubility. The high DP alkylpolyglycoside is generally less water soluble, has higher solution viscosity, and is particularly useful as an additive in personal care products. Any of the three alkylpolyglycoside products of the present invention; i.e. the waxy alkylpolyglycoside product, the high DP alkylpolyglycoside powder, and the low DP alkylpolyglycoside paste, can be added directly to compositions such as detergent formulations and personal care product formulations. A significant advantage is provided over use of other anionic, cationic, and nonionic surfactants in preparing formulations in that the solid alkylpolyglycoside can be added without significantly modifying the viscosity of the formulated composition.

Any of the particular alkylpolyglycoside products of the present invention can be used to form solutions having a wide pH range from about 7.5 to about 12 by adjusting the pH of the solution with appropriate bases. Bases which are useful in adjusting the pH of the aqueous solutions of the alkylpolyglycoside include but are not limited to NaOH, KOH, $Na_2CO_3$, $K_2CO_3$, $MgCO_3$, $Mg(OAc)_2$, MgO, and triethanolamine. Preferred bases include NaOH, triethanolamine, and $Na_2CO_3$.

The following examples are to illustrate the invention but should not be interpreted as a limitation thereon.

EXAMPLES

Materials and Methods

In the following examples, the pre-formed binary $NaHSO_4$ catalyst used was obtained from Aldrich. When the $NaHSO_4$ catalyst was prepared in situ, it was prepared by dissolving the appropriate amount of base in a portion of n-butanol or higher alcohol, thereby forming a metal butoxide, then adding the required portion of $H_2SO_4$. The binary sulfate catalyst composition is illustrated in the examples as a ratio of moles of $H_2SO_4$ to moles of base. Addition of $H_2SO_4$ to the metal butoxide provided a fine white precipitate. The catalyst solutions were stirred for approximately 5 minutes before use. The total catalyst concentration that was utilized in each example is reported as mmol (1/1000 of a mole) of bisulfate/mmol glucose. In the case of in situ preparation of the catalyst, the mmol of bisulfate is based on the mmol of $H_2SO_4$ used to prepare the catalyst.

Color was evaluated on a scale of 1 to 5 with 1 (white, colorless) being the best and 5 (black) being the worst. Surface tension measurements were made using a BYK Gardner Dynometer equipped with a platinum ring. Prior to use, the instrument was calibrated with o-xylene as a standard with a surface tension measurement of 30.1 mN/m at 20° C. Unless indicated, reported surface tensions are for 5% aqueous solutions. The sample DP, average alkyl chain length, and $\alpha/\beta$ ratio was determined by $^1$H NMR. The NMR samples were prepared by dissolving about 20 mg of sample in DMSO-$d_6$ (dimethyl sulfoxide) to which was added about 2 drops of TFA-d prior to recording the sample spectrum.

Example 1

This example illustrates the two-stage process of the present invention.

To a 500 mL three-neck round bottom flask equipped with a mechanical stirrer, distillation column, and addition funnel was added 50 g (277 mmol) of anhydrous glucose, 0.3 g of $NaHSO_4$ (2.5 mmol), and 132 mL of n-butanol. The reaction was heated to reflux and water formed during the reaction was removed by distillation. After 40 minutes at reflux, the reaction was crystal clear and no solids were observed. To the reaction mixture was slowly added a solution of 311 mL of dodecanol (1.39 mol, 5 eq.) containing 35 mL of n-butanol. Twenty minutes into the addition, a vacuum was applied (550 mm Hg) and n-butanol was removed at a rate equal to the addition of the dodecanol/butanol solution (head temperature=90° C.). The vacuum was decreased stepwise during the addition so that when the addition was complete (115 min), the applied vacuum was 120 mm Hg (head temperature=58° C.). After the addition was complete, the applied vacuum was slowly lowered to 0.5 mm Hg (head temperature=118° C.) and the excess alcohol was removed. That provided a slightly hazy, colorless viscous melt (Total reaction time=7.5 hours). The pH of the reaction mixture upon completion of the reaction was 7. After cooling, 87.5 g of a white solid was obtained. Proton NMR of the crude reaction mixture showed that the average alkyl chain length was 12 carbons, the $\alpha/\beta$ ratio was 3.9, and the DP was 1.0. A portion of the crude mixture was washed with $Et_2O$ and analysis by $^1$H NMR of the extracted solid showed an average alkyl chain length of 10, an $\alpha/\beta$ ratio of 4.3, and a DP of 3.0.

Example 2

This example illustrates that the long chain alcohol (dodecanol) can be added as a preheated liquid rather than as a $C_{12}$ ROH/$C_4$—ROH mixture, as was used in Example 1:

To a 500 mL three-neck round bottom flask equipped with a mechanical stirrer, distillation column, and addition funnel was added 50 g (277 mmol) of anhydrous glucose, 0.3 g of $NaHSO_4$ (2.5 mmol), and 132 mL of n-butanol. The reaction was heated to reflux and water formed during the reaction was removed by distillation. After 35 min at reflux, the reaction was crystal clear and no solids were observed. To the reaction mixture was slowly added 311 mL of heated dodecanol (1.39 mol, 5 eq.). Twenty minutes into the addition, a vacuum was applied (550 mm Hg) and n-butanol was removed at a rate equal to the addition of the dodecanol (head temperature=109° C., pot temperature=117° C.). The vacuum was decreased stepwise during the addition so that when the addition was complete (80 min), the applied vacuum was 120 mm Hg (head temperature=69° C., pot temperature=99° C.). After the addition was complete, the applied vacuum was slowly lowered to 0.2 mm Hg (head temperature=111–113° C., pot temperature=117–120° C.) and the excess alcohol was removed which provided a pale yellow viscous melt (Total reaction time=7.8 hours). After cooling, 95.5 g of a white solid was obtained.

Example 3

Following the general procedure described in Example 1, the capability of the binary bisulfate catalyst, relative to p-toluene sulfonic acid and $H_2SO_4$, to catalyze the formation of $C_8$ alkylpolyglycoside and the impact of these catalysts on the product composition and quality was evaluated. The binary bisulfate catalyst was prepared in situ using $H_2SO_4$ and NaOH, according to the general procedure described in methods and materials. The results are summarized in Table I below.

TABLE I

| Catalyst | EQ/C# stage 1 | EQ/C# stage 2 | DP Crude | DP Et$_2$O | C# crude | C# Et$_2$O | Base | CT (hr) | Color | ST (dynes/cm) |
|---|---|---|---|---|---|---|---|---|---|---|
| 0.036 mmol of 0.91/1 H$_2$SO$_4$/NaOH binary cat. | 5.2/C$_4$ | 5.0/C$_8$ | 1.30 | 1.40 | 6 | 6 | None | 1.8 | White, 1 | 24.9 |
| 0.018 mmol PTSA | 5.2/C$_4$ | 5.0/C$_8$ | 0.60 | 1.60 | 8 | 8 | Mg(OAc)$_2$ | 1.0 | black, 5 | 26.0 |
| 0.018 mmol H$_2$SO$_4$ | 5.2/C$_4$ | 5.0/C$_8$ | 0.80 | 5.20 | 8 | 8 | Mg(OAc)$_2$ | 1.0 | black, 5 | — |
| 0.009 mmol H$_2$SO$_4$ | 5.2/C$_4$ | 5.0/C$_8$ | 1.30 | 1.50 | 8 | 8 | Mg(OAc)$_2$ | 1.0 | black, 5 | 27.9 |
| 0.018 mmol PTSA | 5.2/C$_4$ | 5.0/C$_8$ | 2.00 | 3.50 | 8 | 8 | None | 1.0 | black, 5 | 24.7 |
| 0.018 mmol of 0.91/1 H$_2$SO$_4$/NaOH binary cat. | 5.2/C$_4$ | 5.0/C$_8$ | 0.80 | 1.30 | 7 | 7 | Mg(OAc)$_2$ | 1.8 | white, 1 | — |

"C#" - chain length of the alkyl alcohol;
"PTSA" - p-toluene sulfonic acid;
"DP" - number of glucose units per alkyl group;
"EQ" - the base used to neutralize the acid catalyst;
"DP crude" - the DP of the product obtained without additional purification;
"DP Et$_2$O" - the DP of the product after washing the crude product with diethyl ether;
"CT" - Total reaction time;
"ST" - surface tension.

This example illustrates that the 0.91/1 H$_2$SO$_4$NaOH binary sulfate catalyst of the present invention promotes the formation of butyl glycoside of much superior color quality than H$_2$SO$_4$ or PTSA. This example also shows that there is no need to add base to neutralize the binary sulfate catalyst of the present invention. The present process is slightly slower in relation to the H$_2$SO$_4$ and PTSA catalyzed reactions. The surface tensions are similar.

Example 4

This Example illustrates that NaOH is the preferred base in forming the binary bisulfate catalyst of the process of the present invention. The general procedure described in Example 1 was followed. The H$_2$SO$_4$NaOH binary sulfate catalyst was prepared in situ according to the general procedure described in the Materials and Methods section above. The results of the alkylpolyglycoside formed by the process of the present invention are summarized in Table II below.

Example 5

This Example demonstrates that product of high quality can be obtained by the process of the present invention without having to utilize a neutralizing base.

The following examples were prepared using the general procedure described in Example 1. The binary H$_2$SO$_4$/NaOH catalyst was prepared in situ according to the general procedure described in the Materials and Methods section above. Referring to Table III, the example in the second row illustrates that a neutralizing base can be omitted while still obtaining a colorless product with a DP in an acceptable range. In the second example in row 3, the reaction was conducted in the same manner except that the neutralizing base was added to the hot reaction mixture and distillation was continued for an additional 20 min which gave a black product with a noticeable odor; prior to addition of base the reaction mixture was a very pale yellow. In the third example in row 4, the reaction was conducted in the same manner except that the neutralizing base was added to the cool reaction mixture and a 0.1 mm Hg vacuum was applied under mild heating for an additional 20 min.

TABLE II

| Catalyst | EQ/C# stage 1 | EQ/C# stage 2 | DP Crude | DP Et$_2$O | C# crude | C# Et$_2$O | Base | CT (h) | Color | ST (dynes/cm) |
|---|---|---|---|---|---|---|---|---|---|---|
| 0.018 mmol 0.91/1 H$_2$SO$_4$/NaOH | 5.2/C$_4$ | 5.0/C$_8$ | 2.30 | 1.90 | 6 | 6 | None | 1.9 | white, 1 | 26.8 |
| 0.018 mmol 1.07/1 H$_2$SO$_4$/KOH | 5.2/C$_4$ | 5.0/C$_8$ | 1.60 | 2.00 | 8 | 8 | None | 1.0 | brown, 4 | 24.7 |
| 0.018 mmol 0.91/1 H$_2$SO$_4$/LiOH | 5.2/C$_4$ | 5.0/C$_8$ | 1.90 | 2.60 | 8 | 8 | None | 0.8 | black, 5 | 24.6 |

"C#" - chain length of the alkyl alcohol;
"PTSA" - p-toluene sulfonic acid;
"DP" - number of glucose units per alkyl group;
"EQ" - equivalents of alcohol to glucose;
"base" - the base used to neutralize the acid catalyst;
"DP crude" - the DP of the product obtained without additional purification;
"DP Et$_2$O" - the DP of the product after washing the crude product with diethyl ether;
"CT" - Total reaction time;
"ST" - surface tension.

TABLE III

| Catalyst | EQ/C# stage 1 | EQ/C# stage 2 | DP Crude | DP Et$_2$O | C# crude | C# Et$_2$O | Base | CT (h) | Color | ST (dynes/cm) |
|---|---|---|---|---|---|---|---|---|---|---|
| 0.018 mmol 0.91/1 H$_2$SO$_4$/NaOH | 5.2/C$_4$ | 5.0/C$_8$ | 2.30 | 1.90 | 6 | 6 | None | 1.9 | white, 1 | 26.8 |
| 0.018 mmol H$_2$SO$_4$/NaOH | 5.2/C$_4$ | 5.0/C$_8$ | 1.96 | 2.00 | 6 | 6 | Mg(OAc)$_2$ | 2.0 | black, 5 | 30.2 |
| 0.018 mmol 0.91/1 H$_2$SO$_4$/NaOH | 5.2/C$_4$ | 5.0/C$_8$ | 0.80 | 1.30 | 7 | 7 | Mg(OAc)$_2$ | 1.8 | white, 1 | — |

"C#" - chain length of the alkyl alcohol;
"PTSA" - p-toluene sulfonic acid;
"DP" - number of glucose units per alkyl group;
"EQ" - equivalents of alcohol to glucose;
"base" - the base used to neutralize the acid catalyst;
"DP crude" - the DP of the product obtained without additional purification;
"DP Et$_2$O" - the DP of the product after washing the crude product with diethyl ether;
"CT" - Total reaction time;
"ST" - surface tension.

Example 6

This Example illustrates the split addition of the binary sulfate catalyst in the present process. Split addition is an effective means to maintain reaction rate and product quality. The example also illustrates the addition of a nonsolvent to the heated crude product under shear as a means of isolating a high DP alkylpolyglycoside as a white powder and a low DP alkylpolyglycoside as a colorless paste.

The following sample was prepared using the general procedure described in Example 1 with the exception that 0.018 equivalents of a 0.9/1 H$_2$SO$_4$NaOH binary sulfate catalyst was added with the butanol and 0.018 equivalents of a 0.9/1 H$_2$SO$_4$/NaOH binary sulfate catalyst was added with a C$_{12}$ROH. The H$_2$SO$_4$/NaOH catalyst was prepared in situ according to the general procedure described in the Materials and Methods section above. After removing all of the excess alcohol by vacuum distillation, a portion of the product was heated to obtain a viscous melt. To this melt was added acetone while vigorously stirring, thereby providing a white powder. The powder was removed by filtration and dried, giving a white free flowing powder which represented 35% of the original sample. The acetone was removed by vacuum distillation yielding a colorless paste. Table IV below provides analysis of the samples.

TABLE IV

| Sample | DP | α/β | C# | α Color | ST (dynes/cm) |
|---|---|---|---|---|---|
| Crude Product | 1.5 | 3.4 | 9 | | |
| Washed with Et$_2$O | 1.9 | 2.4 | 8 | | |
| Acetone Insoluble | 3.4 | 4.5 | 8 | 87 | 25.6 |
| Acetone Soluble | 1.0 | Na | 9 | 439 | 30.3 |

"DP" - number of glucose units per alkyl group;
"ST" - surface tension;
"C#" - chain length of the alkyl alcohol;

Example 7

The following represents a typical single-stage reaction embodiment of the process of the present invention. It also illustrates the staged addition of glucose.

To a 5 L three-neck round bottom flask equipped with a mechanical stirrer, distillation column, and addition funnel was added 50 g of anhydrous glucose, 3 g of NaHSO$_4$ (25 mmol), and 3.11 L of 1-dodecanol. The reaction was heated to the desired reaction temperature of 115° C. When the reaction temperature reached 100° C., an additional 150 g of glucose was added and the pressure was lowered to 170 mm Hg while providing an air sweep across the surface of the reaction. One hundred minutes after reaching the desired reaction temperature, an additional 150 g of anhydrous glucose was added followed by an additional 150 g at 5 hours after reaching reaction temperature. Nine hours after reaching the reaction temperature, the reaction mixture was a pale yellow, hazy solution with no glucose particles visible. The reaction was filtered to give a faint yellow, clear solution.

This Example demonstrates that the binary bisulfate catalyst is effective in the direct preparation of higher alkyl polyglycosides and illustrates the staged addition of the anhydrous glucose.

Example 8

A C$_{12}$ alkylpolyglycoside was prepared according to the general procedure of Example 7 using 0.009 eqs of NaHSO$_4$ as catalyst. Portions of the crude reaction mixture containing excess dodecanol were passed through a Pope wipe film evaporator which had a 2 inch (5.08 cm) diameter column and an 8 inch (20.32 cm) heating zone at 0.6 mm Hg at three different temperatures (pH=4.5). The pH of a portion of the crude reaction mixture was adjusted to 8 and this portion was also passed through the wipe film evaporator. After removing all of the alcohol, a glassy solid was obtained. The results are shown in Table V.

TABLE V

| Temperature (° C.) | % ROH removed in the first pass | Number of passes required to remove 100% of the ROH | α/β | C# | DP | ST (dynes/cm, 0.5% alkylpolyglycoside) | Color |
|---|---|---|---|---|---|---|---|
| 115 | 52 | 3 | 1.47 | 11.9 | 1.47 | 27.2 | Pale Yellow |
| 135 | 94 | 2 | 1.85 | 11.6 | 1.55 | 29.3 | Pale Yellow |

TABLE V-continued

| Temperature (° C.) | % ROH removed in the first pass | Number of passes required to remove 100% of the ROH | α/β | C# | DP | ST (dynes/cm, 0.5% alkylpolyglycoside) | Color |
|---|---|---|---|---|---|---|---|
| 155 | 100 | 1 | 1.54 | 12.5 | 1.32 | 28.1 | Pale Yellow |
| 155 (pH = 8) | 100 | 1 | 1.92 | 12.3 | 1.25 | 28.5 | Dark Brown |

This example illustrates that the reaction product can be distilled over a wide temperature range using a distillation device such as a wipe film evaporator or falling film evaporator without having to adjust the pH of the reaction mixture to greater than 7. The example in which the pH was adjusted to 8 illustrates that there is a distinct disadvantage in practicing the prior art in which the pH is made basic prior to distillation. In the prior art, the nature of the catalysts made adjustment of the pH to greater than 8 necessary whereas the binary sulfate catalyst of the present invention does not require neutralization prior to distillation. Hence, bleaching with peroxides or other agents is not necessary in the practice of the present invention.

Example 9

Thirty grams of a $C_{12}$ alkylpolyglycoside, prepared according to the general procedure of Example 7 using 0.009 eqs of $NaHSO_4$ as catalyst and passed through a wipe film evaporator at 155° C., was ground in the presence of 200 mL of acetone. The acetone insoluble fraction (61% of the crude material) was isolated by filtration as a fine, free flowing white powder. The acetone soluble portion (39% of the crude material) was concentrated to obtain a yellow paste.

TABLE VI

| Sample | DP | α/β | C# | Color of 1% aqueous solution |
|---|---|---|---|---|
| Crude Product | 1.32 | 1.54 | 12.5 | hazy, colorless solution |
| Acetone Insoluble | 1.79 | 1.67 | 12.6 | crystal clear solution |
| Acetone Soluble | 0.86 | 1.60 | 12.2 | yellow, hazy solution |

This example illustrates that the alkylpolyglycoside obtained after distillation can be further purified by grinding the waxy solid in the presence of a nonsolvent such as acetone to obtain an alkylpolyglycoside which can be handled and utilized in formulations as a powder.

What is claimed is:

1. A process for making an alkylpolyglycoside comprising reacting a monosaccharide with an alcohol having from 2 to 50 carbon atoms selected from the group consisting of primary alcohols, secondary alcohols, and a mixture thereof in the presence of a binary sulfate catalyst under heat, the binary sulfate catalyst comprising a molar ratio of $H_2SO_4$ to inorganic base of about 0.7:1 to 1.1:1, thereby forming an alkylpolyglycoside product.

2. The process of claim 1 wherein the inorganic base is selected from the group consisting of LiOH, NaOH, KOH, $Na_2CO_3$, $K_2CO_3$, and $Li_2CO_3$.

3. The process of claim 1 wherein the molar ratio of $H_2SO_4$ to inorganic base in the binary sulfate catalyst is about 0.85:1 to 1:1.

4. The process of claim 1 wherein the monosaccharide is reacted with the alcohol at a pH of about 4 to 6.5.

5. The process of claim 1 wherein the monosaccharide is selected from the group consisting of glucose, mannose, galactose, talose, altrose, lyose, arabinose, xylose, ribose, fructose, a compound hydrolyzable to a monosaccharide, and a mixture thereof.

6. The process of claim 1 wherein the monosaccharide is reacted with an alcohol having from about 8 to about 50 carbon atoms.

7. The process of claim 1 wherein a molar ratio of binary sulfate catalyst to monosaccharide is about 0.001:1 to 0.5:1.

8. The process of claim 7 wherein the molar ratio of binary sulfate catalyst to monosaccharide is about 0.006:1 to 0.2:1.

9. The process of claim 1 wherein the alcohol is a primary, monohydric, aliphatic alcohol represented by the formula ROH, wherein R is a selected from the group consisting of alkyl groups having about 4 to 18 carbon atoms, alkenyl groups having about 4 to 18 carbon atoms, and a mixture thereof.

10. The process of claim 1 wherein the alcohol is selected from a monohydric alcohol represented by the formula:

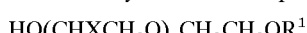

wherein $R^1$ is an alkyl group having about 1 to 20 carbon atoms, X is hydrogen or an aliphatic group having 1 to about 10 carbon atoms, and n is an integer from 0 to about 20.

11. The process of claim 1 wherein the alcohol is a polyhydric alcohol.

12. The process of claim 1 wherein the alcohol is reacted with the monosaccharide at a molar ratio of about 1.5:1 to 10:1 alcohol to monosaccharide.

13. The process of claim 12 wherein the molar ratio of the alcohol to the monosaccharide is about 3:1 to 6:1.

14. The process of claim 1 wherein the monosaccharide is reacted with an alcohol having about 2 to 4 carbon atoms at a molar ratio of alcohol to monosaccharide of about 3:1 to 6:1 to form a $C_2$- to $C_4$-alkylpolyglycoside, further comprising reacting the $C_2$- to $C_4$-alkylpolyglycoside product with an alcohol having about 8 to 50 carbon atoms at a molar ratio of alcohol to $C_2$- to $C_4$-alkylpolyglycoside of about 3:1 to 6:1.

15. The process of claim 1 wherein the monosaccharide is reacted with the alcohol at a temperature of about 90 to 150° C.

16. The process of claim 1 further comprising the step of removing a sufficient amount of unreacted alcohol from the alkylpolyglycoside product thereby forming a waxy alkylpolyglycoside product containing less than 5 weight percent unreacted alcohol.

17. The process of claim 16 wherein the alkylpolyglycoside product is formed in the absence of base to neutralize acid.

18. A detergent or personal care product formulation comprising the waxy alkylpolyglycoside product produced by the process of claim 16 or 17.

* * * * *